United States Patent [19]
Park et al.

[11] Patent Number: 5,871,708
[45] Date of Patent: *Feb. 16, 1999

[54] RADIOACTIVE PATCH/FILM AND PROCESS FOR PREPARATION THEREOF

[75] Inventors: Kyoung Bae Park; Jae-Rock Kim; Jong-Du Lee, all of Seoul, Rep. of Korea

[73] Assignee: Korea Atomic Energy Research Institute, Daejeon-si, Rep. of Korea

[*] Notice: This patent issued on a continued prosecution application filed under 37 CFR 1.53(d), and is subject to the twenty year patent term provisions of 35 U.S.C. 154(a)(2).

[21] Appl. No.: 610,554

[22] Filed: Mar. 6, 1996

Related U.S. Application Data

[63] Continuation-in-part of Ser. No. 498,346, Jul. 5, 1995, abandoned.

[30] Foreign Application Priority Data

| | | | |
|---|---|---|---|
| Mar. 7, 1995 | [KR] | Rep. of Korea | 1995-4642 |
| Feb. 29, 1996 | [KR] | Rep. of Korea | 1996-5322 |

[51] Int. Cl.$^6$ .............................. A61K 51/12; A61N 5/00; A61L 3/00
[52] U.S. Cl. ........................ 424/1.25; 424/1.11; 424/449; 600/1; 427/2.31
[58] Field of Search ................................. 424/1.11, 1.25, 424/1.29, 1.33, 449; 600/2, 3, 4, 5, 6, 7, 8, 1; 427/2.31; 252/505, 517, 625

[56] References Cited

U.S. PATENT DOCUMENTS

| | | | |
|---|---|---|---|
| 4,889,707 | 12/1989 | Day et al. | 424/1.1 |
| 4,946,435 | 8/1990 | Suthanthiran et al. | |
| 5,030,195 | 7/1991 | Nardi | 600/7 |
| 5,342,283 | 8/1994 | Good | |

OTHER PUBLICATIONS

Andrews et al., "Hepatic Radioembolization with Yttrium–90 Containing Glass Microspheres: Preliminary Results and Clinical Follow–up", Journal of Nuclear Medecine 1994, vol. 35, pp. 1637–1646.

Mumper et al., "Neutron–Activated Holmium–166–Poly (L–Lactic Acid) Microspheres: A Potential Agent for the Internal Radiation Therapy of Hepatic Tumors", Journal of Nuclear Medicine 1991, vol. 32, pp. 2139–2143.

Will et al., "Comparison of Two Yttrium–90 Regimens in Inflammatory and Osteoarthropathics", Annals of the Rheumatic Diseases 1992, vol. 51, pp. 262–265.

Chinol et al., "Chemistry and Biological Behavior of Samarium–153 and Rhenium–186–Labeled Hydroxyapatite Particles: Potential Radiopharmaceuticals for Radiation Synovectomy", Journal of Nuclear Medicine, 1993, vol. 34, pp. 1536–1542.

Knorr, "Functional Properties of Chitin and Chitosan", Journal of Food Science 1982, vol. 47, pp. 593–595.

Hnatowich et al., "Dysprosium–165 Ferric Hydroxide Macroaggregates for Radiation Synovectomy", Journal of Nuclear Medecine 1977, vol. 19, No. 3, pp. 303–308.

(List continued on next page.)

Primary Examiner—Gary E. Hollinden
Assistant Examiner—Michael G. Hartley
Attorney, Agent, or Firm—Dilworth & Barrese

[57] ABSTRACT

This invention relates to a radioactive patch/film and process of preparation thereof. The radioactive patch/film containing radioactive material can irradiate on skin directly. The radioactive patch/film is prepared by the process, wherein, various forms of the patch/film containing stable nuclide is prepared and irradiated with neutrons. The patch/film is very effective to treat various kinds of cancers, and dermal diseases.

28 Claims, 2 Drawing Sheets

OTHER PUBLICATIONS

Wang et al. "Preparation and Biodistribution of Yttrium–90 Lipiodol in Rats Following Hepatic Arterial Injection", European Journal of Nuclear Medicine, Mar. 1995, vol. 22, No. 3, pp. 233–236.

McLaren et al., "Dyprosium ($^{165}$Dy) Hydroxide Macroaggregates for Radiation Synovectomy–Animal Studies", European Journal of Nuclear Medicine 1990, vol. 16, pp. 627–632.

Clunie et al., "Samarium–153–Particulate Hydroxyapatite Radiation Synovectomy: Biodistribution Data for Chronic Knee Synovitis", Journal of Nuclear Medicine 1995, vol. 36, pp. 51–57.

RADIOACTIVE PATCH/FILM AND PROCESS FOR PREPARATION THEREOF

This is a continuation-in-part of application Ser. No. 08/498,346 filed Jul. 5, 1995 now abandoned.

TECHNICAL FIELD

The present invention relates to a radioactive patch/film, a novel type for irradiating in the field of an external radiation therapy, and process for preparation thereof.

In particular, the present invention relates to a patch/film, which can be attached to patient's skin or mucous membrane to treat the lesions by direct irradiation.

And the present invention relates to the process for preparation of a radioactive patch/film, wherein 1) to prepare the radioactive patch; particles of stable nuclide mixed with adhesive agent are coated on the carrier, laminated for sealing, and then irradiated with neutrons in the nuclear reactor and 2) to prepare the radioactive film; the solution of stable nuclide mixed with the solution of adhesive agent are made into the thin membrane, dried, laminated for sealing and then irradiated with neutrons in the nuclear reactor.

BACKGROUND OF ART

There are two kinds of radiation therapy; one is the internal radiation therapy that radioactive material is administered into the lesion to emit radiation in the human body, and the other is the external radiation therapy that radiation is emitted from the outside of the body through special equipments.

In the internal radiation therapy, radioactive materials are administered orally, intravenously or by injecting directly into the body. But the internal radiation therapy has not yet been utilized widely on the reason that a radioactive material administered to the lesion may be leaked out and spread to the whole body through blood flow, and accumulated to other organs or tissues, and it results in a fatal damage to other organs, especially bone marrow very sensitive to radiation. Therefore, most malignant tumors have been treated by the external radiation therapy.

The external radiation also has many problems. For the external radiation therapy, radionuclides with high penetrative radiation should be used, since the rays are emitted out of the body, and it results in the irradiation of adjacent normal tissue as well as the lesion. And it is not convenient to use the external radiation on account of expensive equipments, hospitalization and the like.

The inventors have conducted intensive research in order to find the way of irradiating the lesion conveniently and invented the new therapeutic type for irradiation to patients. That is, radioactive material is prepared in a form of patch/film which makes irradiation easy and irradiates lesion site specifically.

SUMMARY OF THE INVENTION

The object of the present invention is to provide the radioactive patch/film for the external radiation therapy.

The radioactive patch of the present invention is prepared by the process, wherein the particles of stable nuclide mixed with adhesive agent are coated on the carrier, laminated for sealing to form the patch, and then irradiated with neutrons in the nuclear reactor to convert the patch into the radioactive patch.

The radioactive film of the present invention is prepared by the process, wherein the stable nuclide mixed with the solution of adhesive agent are made into the thin membrane, dried, laminated for sealing to form the film, and then irradiated with neutrons in the nuclear reactor to convert the film into the radioactive film.

And the object of the present invention is to provide the use of the radioactive patch/film as pharmaceutical agent for the external radiation therapy. The radioactive patch/film is attached to skin or mucous membrane and it irradiates lesion site directly.

And the object of the present invention is to provide the radioactive patch/film which irradiates only the lesion site without damage of the adjacent normal tissue, since the shape and the size of the patch/film are controlled according to those of the lesion.

And the object of the present invention is to provide the radioactive patch/film in which the irradiation dose can be controlled by amount of particles and their radioactivity.

The present invention will be described in detail in the following.

BRIEF DESCRIPTION OF THE DRAWINGS

FIG. 2 shows the recovery of tumor by treatment of the radioactive patch of this invention;

FIG. 2C shows the recovery of skin cancer after 1 week of the treatment, with

DETAILED DESCRIPTION OF THE PREFERRED EMBODIMENTS

Figure 1A:
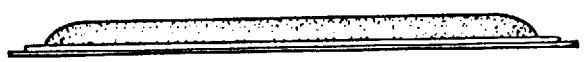
FIGS. 1(A) and 1(B) are respectively side elevational and top plan views showing the radioactive patch prepared by the process of this invention.

The representative diseases which can be treated with the radioactive patch/film of the present invention are skin diseases. In the following, the radioactive patch/film will be described in detail in the view of treatment of dermal disease, especially skin cancer. But it is evident this patch/film can be used for other diseases which can be treated by the radiation therapy.

Skin cancer is a popular disease to prime age and old age, and it is developed by exposing to sunlight, pollution material, carcinogen, radiation and the like and also by chronic skin ulcer, burn and the like. The incidence of cancer disease is dependent on races, individuals and nations, but high in white people. For example, it is reported that in Canada skin cancer is developed in 39 persons out of 100,000 persons. For the treatment of skin cancer, one of the most common malignant tumor to human beings, lesion burning, irradiation or surgical therapy are often used.

But the surgical therapy of skin cancer has some troubles. The surgical therapy is impossible when the cancer is developed in the site impossible to be operated. Even if the surgical therapy is possible, the radiation therapy is preferred than the surgical therapy for skin cancer, since the skin cancer is often developed in multiple sites, and skin-grafting accompanied after surgical operation are not easy.

The effect of the radiation therapy is affected remarkably by total irradiation dose, divisional radiation, radiation range, property of radiation and the like.

Hitherto, X-rays, megavoltage electron rays or γ-ray has been used in the treatment of malignant skin cancer. Generally 5,000–10,000 rad is optimal as total irradiation dose and this total dose should be divided and irradiated by each 200–350 rad for about 4–6 weeks. The reason to irradiate the total irradiation dose in divisional pattern is to minimize the damage to the adjacent normal tissue or organ by X-rays, electron rays, γ-rays of high energy. The external radiation therapy has been widely used, since it leads to relatively good results, but there remains some demerits. Long-reaching radiation tends to damage adjacent organs such as bones, cartilage and the like, and the treatment takes long on account of divisional irradiation and has some difficulties because of expensive equipments and hospitalization.

Therefore the inventors of the present invention have completed this invention to overcome the demerits aforementioned. That is, to prepare the radioactive patch, particles of stable nuclide emitting high-energy (1.4–2.2 MeV) β-ray or γ-ray are mixed with adhesive agent, coated on the carrier, laminated with polyethylene film for sealing, and then irradiated with neutrons in the nuclear reactor. And to prepare the radioactive film, the stable nuclide emitting β-ray or γ-ray is mixed with the solution of adhesive agent, made into thin membrane, dried, laminated with polyethylene film for sealing and then irradiated with neutrons in the nuclear reactor.

The radioactive patch/film of this invention has many merits to treat dermal diseases as described below. The radioactive patch/film uses β-rays, differently from previously established method using X-rays, electron rays and γ-rays, and hence adjacent organs, especially bone or bone marrow, are safe in spite of irradiation. And as the total irradiation dose, 5,000–10,000 rad can be irradiated at one time. Therefore the period of irradiation reduces to 1–2 hrs, compared with about 4–6 weeks of the previous method and the period of attending hospital also reduces much. The used radionuclide decays soon due to short half-life of β-emitter such as 1–3 days.

Skin cancer developed in multiple sites can be treated simultaneously by using the radioactive patch/film of the present invention. Since the shape and the size of the patch/film are controlled according to those of lesions, the lesions which are located in the site difficult to be operated, or the lesions which are too large to be operated can be treated. The radioactive patch/film containing the required amount of radioactivity according to the diseases can be easily made, since the radioactivity of patch/film is in proportion to the size and the amount of the contained particles.

Since the irradiation of the normal site can be prevented by irradiating only the lesion and by blocking the normal site with aluminum foil where the radioactive patch/film are attached, there is no side effect such as damage to bone or cartilage, or over-irradiation of other organs caused by the known method.

And the irradiation of the normal site also can be prevented by using the patch/film blocked on one side in case of the treatment of rubbing part of the body, such as armpit, groin and the like.

In addition, the radioactive patch/film of this invention can be applied in several patterns, wherein the patch is used in monolayer and multilayer and the film is used in spread pattern or tube pattern.

In the following, the process to prepare the radioactive patch/film of this invention will be described.

This invention relates to the radioactive patch/film which contains radioactive materials in a form of tape.

General patches need to satisfy the requirements described as below. To administer medicine into the body through skin, the absorption ratio of effective component is very important since skin prevents foreign substances from absorption, and hence absorption-enhancer should be mixed with adhesive agent. In addition, the effective substance should not react with adhesive agent, absorption-enhancer and the like.

Therefore it is important to choose the adhesive agent, absorption-enhancer and the like satisfying the above requirements according to the effective substance to be administered.

Since the layer of adhesive agent is contact directly with skin for some time, the metabolism of skin is liable to be inhibited, which can provoke side effects such as red spot, dropsy and the like. Hence it is desirable that adhesive agent material does not remain in the lesion site after removal of the tape.

However, in case of the radioactive patch/film, first, absorption enhancer or the like is not necessary since the purpose of the patch/film is only irradiation, not administration of pharmaceutical agents, secondly, the selection of adhesive agent is not limited and most of adhesive agent can be used in this invention, since it is used for irradiation itself by radioisotope and chemical reaction has no effect on irradiation dose. In addition the radioactive material used in this invention does not contaminate environment since radionuclide on the patch/film has short half-life.

The adhesive agents which can be used in this invention are urethane series, acryl series, chloroprene series, polyvinylalcohol (PVA) series, polyvinylchloride (PVC) series, nylon series and the like. Besides, all the adhesive agent to be used for preparing patches can be used in the present invention.

The ratio of radionuclide and adhesive agent is 1–30% in a weight ratio preferably. That is, the concentration of radionuclide is controlled in the range of 1–30% preferably.

The radionuclides which used in this invention can be α-emitting radionuclide, β-emitting radionuclide, γ-emitting radionuclide and the like. All the radionuclide for the radiation therapy can be within the scope of the present invention. The nuclide can be selected according to the purpose of the treatment.

In particular, β-emitting radionuclide is preferred in the radioactive patch/film for treating dermal diseases, since β-emitting isotope has an advantage that it damages only the lesion site, not other tissue due to low permeability. The patch/film emitting β-ray is an excellent therapeutical agent, since the permeability of β-ray is so low that it does not reach the normal tissue below the cancer tissue.

In the experiment using $^{166}$Ho-radioactive patch/film, the inventors have found that the excessive irradiation dose damaged only 8 mm of tissue on the maximum and cartilage or bones are not damaged at all.

But in case of thick skin cancer γ-emitting radionuclide is preferred. $^{192}$Ir is γ-emitting radionuclide by which dermal disease can be treated.

In β-emitting radionuclides there are $^{198}$Au, $^{90}$Y, $^{186}$Re, $^{32}$P, $^{169}$Er, $^{166}$Ho, $^{153}$Sm, $^{165}$Dy and the like. According to the purpose of the treatment a radionuclide can be selected.

$^{198}$Au also emits γ-ray abundantly and has a half-life of 2.7 days. $^{32}$P and $^{90}$Y emit only β-ray without emitting γ-ray and have a relatively long half-life.

Radionuclides of Lanthane series comprising $^{165}$Dy, $^{166}$Ho, $^{153}$Sm and $^{169}$Er emit β-ray along with low-energy γ-ray, and have a very short half-life. They have a merit that the stable nuclides of Lanthane series can be easily converted to radionuclides because they can absorb a lot of neutrons when they are irradiated in the nuclear reactor.

Figure 1B:
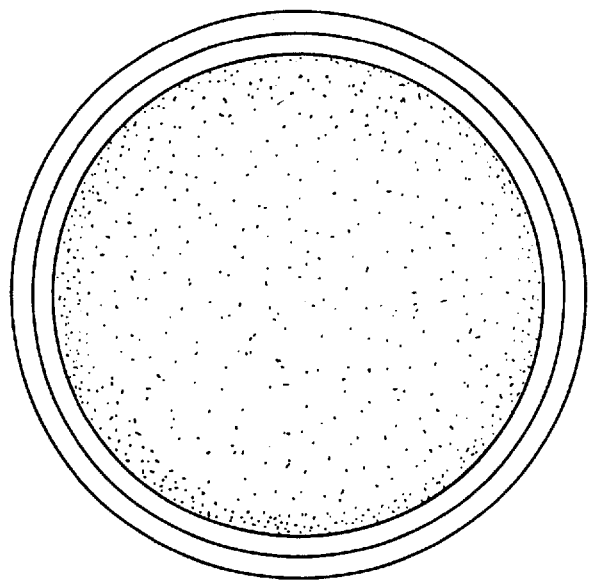

The radioactive patch, as shown in FIG. 1, is prepared according to the steps as follows.

Stable nuclides are made into particles, mixed with adhesive agent, coated on the carrier, laminated for sealing to form the patch, and then the patch is irradiated with neutrons in the nuclear reactor to convert the patch into the radioactive patch. Also, particles of stable nuclide are spread on adhesive tape, laminated for sealing to form the patch, and then irradiated the patch with neutrons in the nuclear reactor to convert into the radio active patch.

Particles of stable nuclide can be prepared by the established method as follows. Preferably its size is 1–10 $\mu$m. To prepare particles of stable nuclide, $^{165}Ho(NO_3)_3 \cdot 5H_2O$ or $^{165}HoCl_3$ is dissolved in distilled water, added $NaBH_4$ in sodium hydroxide, precipitated and then the precipitate is made to pieces by ultra-sonication. In addition particles of stable nuclide also can be prepared by use of $^{164}Dy(NO)_3$ or $^{164}DyCl_3$.

The carrier used in this invention can be paper, textile, metal, plastic film or laminate. Besides, all the carrier can be utilized in the preparation of patches.

The radioactive film is prepared according to the steps as follows.

The stable nuclide is mixed with adhesive agent dissolved in solvent, made into the thin membrane, dried, laminated for sealing to form the film and then irradiated the film with neutrons in the nuclear reactor to convert into the radioactive film. Any stable nuclide compound which is soluble can be used for preparing the radioactive film. Especially $^{164}Dy(NO_3)_3$ or $^{165}Ho(NO_3)_3$ is preferred.

As the adhesive agent utilized to prepare the radioactive film, there are urethane series, acryl series, chloroprene series, PVA series, PVC series, nylon series and the like. As the adhesive agent used in this invention elastic one is preferred, since it makes exercise possible even after attachment.

The adhesive agent of this invention should be dissolved in solvent to prepare the radioactive film. Here all the solvent which can dissolve the adhesive agent can be used. Especially dimethyl-formamide or tetrahydrofuran is preferred.

As the sealing agent utilized to prepare the radioactive patch/film, there are polyethylene, cellulose ester, polysulphonate and the like, most preferably polyethylene or its derivative.

The quality and the efficacy of the radioactive patch and the radioactive film are same but the processes of preparation are different a little.

That is, the radioactive patch is prepared by the process, wherein particles of stable nuclide is mixed with adhesive agent, coated on the carrier, laminated with polyethylene film for sealing, and then the patch is irradiated with neutrons in the nuclear reactor. The radioactive film is prepared by the process, wherein stable nuclide is mixed with the solution of adhesive agent, dried, laminated with polyethylene film for sealing, and then irradiated with neutrons in the nuclear reactor.

In the present invention, the radioactive patch/film can be prepared by irradiating the stable-nuclide patch with neutrons in the nuclear reactor after preparing the stable-nuclide patch in advance.

Such a post-irradiation method can reduces the irradiation of the workers.

In the treatment of the radioactive patch/film, preferably 5,000 rad should be irradiated on tumor lesion. Radiation absorption dose is expressed as formula illustrated as below.

$$D = A\Sigma\Phi i(rk \leftarrow rh)\Delta i$$

$$\Delta i = 2.13 \ NiEi.g.rad/\mu Ci.hr$$

where
D:total absorbed dose (g.rad)
A:accumulated activity ($\mu$Ci)
$\Delta$:equilibrium absorbed dose constant
Ni:number emitted per disintegration
Ei:the average energy of the emission
$\Phi i(rk \leftarrow rh)=1$ in $\beta$particle To utilize the above formula, absorption dose is determined according to volume and weight of tissue. The weight of irradiated site is calculated as formula as below.

$$V = \pi r^2 h$$

In this formula r is a radius of patch/film.

The following examples will further illustrate the present invention, which by no means limit the present invention.

<EXAMPLE 1>

Preparation of $^{166}$Ho-radioactive patch

1) Preparation of $^{165}$Ho-particle ($^{165}$Ho-macroaggregate, $^{165}$HMA)

60 mg of $^{165}Ho(NO_3)_3 \cdot 5H_2O$ or $^{165}$ $HoCl_3$ was dissolved in 0.4 ml of distilled water, then 200 mg of $NaBH_4$ dissolved in 2 ml of 2N NaOH was added to produce hydrogen vigorously and to precipitate simultaneously. The precipitate was pulverized by ultra-sonication for 2 minutes to generate 1–5 $\mu$m pieces. Then it was centrifuged, washed five times with 5 ml of distilled water, also with 5 ml of acetone twice and dried in room temperature.

2) Preparation of $^{165}$Ho-patch $^{165}$Ho particles prepared according to Example 1 (1) was well mixed on a weight basis with 10% adhesive agent (urethane series, acryl series, chloroprene series, polyvinylalcohol series, polyvinylchloride series, nylon series), then the mixture is coated on one side of thin paper, to prepare circular patch of 1 cm in diameter. And both side of the patch was laminated with polyethylene film for particles not to leak out of the film.

3) Preparation of $^{166}$Ho-radioactive patch.

$^{165}$Ho-patch prepared according to Example 1 (2) was irradiated as target material in the nuclear reactor to obtain 4–6 mCi of the radioactive patch. In the nuclear reactor the neutron flux is $1 \times 10^{13} \sim 1 \times 10^{14}$ n/cm$^2$·sec.

<EXAMPLE 2>

Preparation of $^{165}$Dy-radioactive patch

1) Preparation of $^{164}$Dy-particles

The same method as Example 1 (1) described above was performed using $^{164}Dy(NO_3)_3$ or $^{164}DyCl_3$ compounds.

2) Preparation of $^{164}$Dy-patch

The same method as Example 1 (2) described above was performed using $^{164}$Dy particle prepared according to Example 2 (1).

3) Preparation of $^{165}$Dy-radioactive patch

The same method as Example 1 (3) was performed using $^{164}$Dy- patch prepared according to Example 2 (2).

<EXAMPLE 3>

Preparation of $^{90}$Y-radioactive patch

The same method as Example 1 (2), (3) was performed using $^{89}$Y$_2$O$_3$ minute powder.

<EXAMPLE 4>

Preparation of $^{32}$P-radioactive patch

The same method as Example 1 (2), (3) was performed using red phosphorus minute powder.

<EXAMPLE 5>

$^{192}$Ir-radioactive patch

The same method as Example 1 was performed using $^{191}$IrCl$_4$ or $^{191}$Ir(IV) compound.

<EXAMPLE 6>

Preparation of $^{166}$Ho-radioactive film

1) Preparation of $^{165}$Ho-film

Solution in 2 ml of dimethyl formamide (DMF) and 10 ml of tetrahydrofuran (THF) and 1.2 g of polyurethane corresponding to 10% (w/v) of total solution was added and shaken vigorously to dissolve and again 1.2 g of $^{165}$Ho(NO$_3$)$_3$·5H$_2$O corresponding to 10% (w/v) of total solution was added to dissolve completely. 3 ml of solution containing 1.6 mg of pure Ho per 1 cm$^2$ was spread on 70 cm$^2$ flat glass dish which lay on the level. At room temperature the clear solution was left for 1 hr, dried and then baked in oven at 80° C. for 3 hrs. After drying $^{165}$Ho-polyurethane membrane was separated from glass dish carefully by needle and pincette and then the circular patch having 1 cm in diameter was cut by borer. This patch was laminated on the both side by polyethylene film.

2) Preparation of $^{166}$Ho-radioactive film $^{165}$Ho-film prepared according to Example 6 (1), which contained 1.2 mg of pure Ho having 1 cm in diameter, was irradiated as target material in the nuclear reactor to obtain 4–6 mCi of the radioactive films respectively. In the nuclear reactor the neutron flux is $1 \times 10^{13} \sim 1 \times 10^{14}$ n/cm$^2$·sec.

<EXAMPLE 7>

Preparation of $^{165}$Dy-radioactive film

1) Preparation of $^{164}$Dy-film

The same method as Example 6 (1) was performed using Dy(NO$_3$)$_3$.

2) Preparation of $^{165}$Dy-radioactive film

The same method as Example 6 (2) was performed using $^{164}$Dy-film prepared according to Example 7 (1).

<EXAMPLE 8>

Stability test of the radioactive patch/film

Each radioactive patch/film within water of beaker was stirred vigorously by magnetic stirrer and particles or radioactivity leaked out of the patch/film were measured at a time interval by detector. But no particle or no radioactivity was detected in water.

<EXAMPLE 9>

Efficacy test of the radioactive patch/film

1) Animal test

Figure 2A:
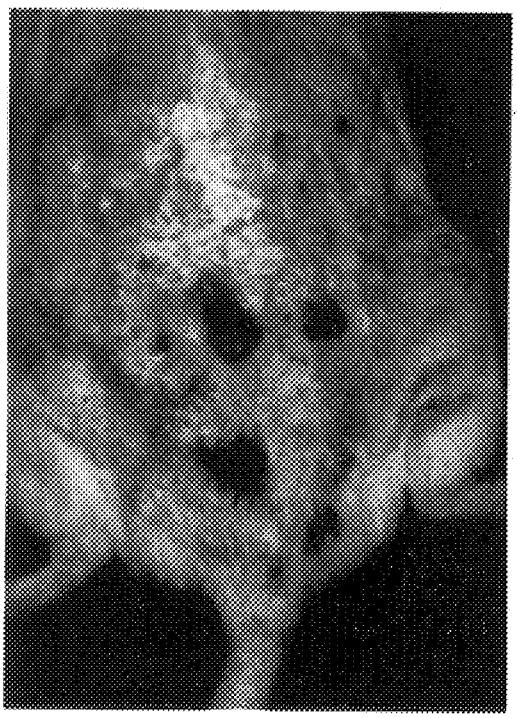
FIG. 2A shows skin cancer in ICR mouse before the treatment.
Figure 2B:
FIG. 2B shows $^{166}$Ho-radioactive patch attached on the lesion of skin cancer.
Figure 2C:
Figure 2D:
FIG. 2D showing condition before treatment.

Skin cancer was induced to ten ICR mice, as shown in FIGS. 2(A)–(B). 12-o-tetradecanoyl-13-acetate dissolved in 0.1 ml of acetone was applied on the skin twice a week and 2'-(4-nitrophenoxy) oxirane dissolved in acetone once a week was applied on the skin for 35 weeks, which induced skin cancer of which the size was about 3–5 mm in diameter. Squamous cell carcinomas in 3 mice and keratoacanthomas in 7 mice were developed. The tumor size was 4–8 mm in diameter and 3–4 mm in thickness.

0.6 mCi of $^{166}$Ho-radioactive patch (0.5 cm in diameter) was attached to lesion site for 1–2 hrs and consequently 7,000–8,000 rad of dose was irradiated. Then the practical radiation absorption dose of tumor was estimated about 45 by measuring TLD. Approximately 350 rad was absorbed by tumor practically. After 1, 4 and 7 weeks, the lesion site of all animals was subjected to pathologic examination. The disappearance of tumor cells, regeneration of epithelial cell and damage of the adjacent tissue by over-exposure were examined by H-E staining. After 1 week of exposure, the disappearance of tissue and the protection of normal tissue characterized in β-ray were found remarkably. An acute dermatitis by irradiation was induced, but it was gradually healed with the regeneration of epithelial cell and tumor was identified to disappear completely by pathologic examination. Even by over-exposure, only 8 mm of tissue on the maximum was damaged and cartilage and bone below the lesion were never affected.

2) Clinical Test

In two patients with squamous cell carcinoma and basal membrane cancer respectively, $^{166}$Ho-radioactive film containing 9–15 mCi was attached to the lesion site for 30–45 minutes. Consequently after 1 week of attachment tumor was identified to disappear.

As described above, the radioactive patch/film of this invention is a novel type of radiation pharmaceutical agent. Without expensive equipment, it is utilized conveniently for the radiation therapy. The period of treatment is short, since enough irradiation can be conducted even in one time exposure. And lesions inaccessible by surgical therapy and multiple sites of cancer are also treated by the patch/film of this invention. It is also an outstanding pharmaceutical agent which irradiates only the lesion site without damage of the adjacent normal tissue, since β-ray emitting radionuclides with low penetrative radiation is utilized to irradiate the lesion at the shortest distance.

And the process of preparation can reduce the irradiation of workers, since stable nuclide is converted to radioisotope after completing the preparation of pharmaceutical agent.

The radioactive patch/film is very effective to treat various kinds of cancer. Especially the radioactive patch/film using β-emitting isotope is very effective to treat skin cancer. In the case of thick skin cancer, γ-emitting isotope is also effective.

The radiation dose at one time is different according to disease and its state, but 5,000–10,000 rad is preferable. The radioactive patch/film in which the radiation dose is controlled in the range of 5,000–10,000 rad or 9–15 mCi, can be attached at the lesion site for about 30 min–3 hrs for the radiation therapy.

What is claimed is:

1. A radioactive patch comprising a carrier, a layer of a mixture of a radionuclide with a nonreactive adhesive agent coated thereon in the form of a tape, and a laminating layer, wherein the adhesive agent is selected from urethane series, acryl series, chloroprene series, PVC series, PVA series and nylon series.

2. A radioactive film comprising a layer of a mixture of a radionuclide with a nonreactive adhesive agent in the form of a tape or membrane, and a laminating layer, wherein the adhesive agent is selected from urethane series, acryl series, chloroprene series, PVC series, PVA series and nylon series.

3. The radioactive patch according to claim 1 wherein the radionuclide is $\beta$-ray emitting nuclide or a $\gamma$-ray emitting nuclide.

4. The radioactive patch according to claim 3, wherein the $\beta$-ray emitting nuclide can be selected from the group comprising $^{153}$Sm, $^{165}$Dy, $^{166}$Ho, $^{32}$P, $^{90}$Y and $^{169}$Er.

5. The radioactive patch application according to claim 3, wherein the $\gamma$-ray emitting nuclide is $^{192}$Ir.

6. A process of preparing the radioactive patch of claim 1, comprising the steps of:
  1) coating a carrier with particles of a stable nuclide mixed with the adhesive agent to prepare the tape,
  2) laminating the tape with a thin membrane for sealing; and
  3) irradiating the sealed tape with neutrons in a nuclear reactor to convert the stable nuclide into the radionuclide which emits radiation.

7. The process of preparing the radioactive patch according to claim 6, wherein the particles of the stable nuclide are selected from the group comprising $^{165}$Ho compounds, $^{164}$Dy compounds, $^{89}$Y$_2$O$_3$, $^{31}$P, and $^{191}$Ir compounds.

8. The process of preparing the radioactive patch according to claim 6, wherein the size of the particles of the stable nuclide is 1–10 $\mu$m.

9. A process of preparing the radioactive film of claim 2, comprising the steps of:
  1) mixing a solution of a stable nuclide with the adhesive agent dissolved in a solvent into a thin membrane and drying the membrane;
  2) laminating the membrane for sealing; and
  3) irradiating the sealed membrane with neutrons in a nuclear reactor to convert the stable nuclide into the radionuclide for emitting radiation.

10. The process of preparing the radioactive film according to claim 9, wherein the stable nuclide is mixed with a solution of $^{165}$Ho(NO$_3$)$_3$ or $^{164}$Dy(NO$_3$)$_3$ dissolved in a solvent.

11. The process of preparing the radioactive patch according to claim 6, wherein the lamination membrane is polyethylene.

12. The radioactive patch according to claim 1, wherein the radioactive patch is used as a pharmaceutical agent for cancer therapy.

13. The radioactive patch according to claim 1, wherein the radioactive patch is used as a pharmaceutical agent for treatment of dermal diseases.

14. The radioactive patch according to claim 13, wherein the dermal disease is skin cancer, water-eczema or keloid.

15. The radioactive film according to claim 2, wherein the radionuclide is a $\beta$-ray emitting nuclide or a $\gamma$-ray emitting nuclide.

16. The process of preparing the radioactive patch according to claim 7, wherein the size of the particles of the stable nuclide is 1–10 $\mu$m.

17. The process of preparing the radioactive patch according to claim 9, wherein the lamination membrane is polyethylene.

18. The radioactive film according to claim 15, wherein the $\beta$-ray emitting nuclide can be selected from the group comprising $^{153}$Sm, $^{165}$Dy, $^{166}$Ho, $^{32}$P, $^{90}$Y and $^{169}$Er.

19. The radioactive film according to claim 15, wherein the $\gamma$-ray emitting nuclide is $^{192}$Ir.

20. The radioactive film according to claim 2, wherein the radioactive film is used as a pharmaceutical agent for cancer therapy.

21. The radioactive film according to claim 2, wherein the radioactive film is used as a pharmaceutical treatment for dermal diseases.

22. The radioactive film according to claim 21, wherein the dermal disease is skin cancer, water-eczema or keloid.

23. The radioactive patch according to claim 1, wherein said layer of nuclide/adhesive agent is coated upon said carrier.

24. The radioactive film according to claim 2, wherein said layer of nuclide/adhesive agent is formed as a thin membrane.

25. The radioactive patch according to claim 23, wherein both sides of said patch are laminated.

26. The radioactive film according to claim 24, wherein both sides of said film are laminated.

27. The radioactive patch according to claim 1, wherein concentration of said radionuclide is approximately 1–30% by weight of said mixture of radionuclide and adhesive agent.

28. The radioactive film according to claim 2, wherein concentration of said radionuclide is approximately 1–30% by weight of said mixture of radionuclide and adhesive agent.

* * * * *